United States Patent [19]
Gauthier et al.

[11] Patent Number: 4,694,113
[45] Date of Patent: Sep. 15, 1987

[54] DUAL CATALYST SEQUENTIAL METHOD FOR PRODUCTION OF SORBITOL FROM HYDROLYZED STARCH SOLUTION

[75] Inventors: George J. Gauthier, Groton; John D. Miceli, New London, both of Conn.

[73] Assignee: Pfizer Inc., New York, N.Y.

[21] Appl. No.: 870,462

[22] Filed: Jun. 4, 1986

[51] Int. Cl.$^4$ .................. C07C 29/132; C07C 29/14; C07C 31/26
[52] U.S. Cl. ...................... 568/863; 568/868
[58] Field of Search .......................... 568/863

[56] References Cited

U.S. PATENT DOCUMENTS

| | | | |
|---|---|---|---|
| 2,868,847 | 1/1959 | Boyers | 260/635 |
| 3,963,789 | 6/1976 | Kruse | 260/635 |
| 4,017,363 | 4/1977 | McMullen | 195/31 R |

FOREIGN PATENT DOCUMENTS

| | | | |
|---|---|---|---|
| 3144320 | 5/1983 | Fed. Rep. of Germany . | |
| 0106630 | 7/1982 | Japan | 568/863 |

OTHER PUBLICATIONS

Faith, Keyes and Clark's Industrial Chemicals, Wiley-Interscience Publn., New York, Fourth Edition, 1975, pp. 774–778.
Starch Conversion Technology, Macel Dekker, Inc., New York, van Beynum and Roels, editors, pp. 278–280, 1985.

Primary Examiner—J. E. Evans

[57] ABSTRACT

A process for production of sorbitol from 50–98.5 DE hydrolyzed starch solution by hydrogenation over a nickel catalyst at a pH of from 3.0 to 7.0, 120° to 160° C. and 500 to 2000 psig (35 to 140 Bars) until the reducing sugar value is below 5 percent; removal of nickel catalyst, acidification to pH 1.0 to 2.5 and hydrogenation of the acidified solution over a ruthenium catalyst, 100° to 180° C. and 500 to 2000 psig, until hydrogen uptake is substantially complete, and removal of the ruthenium catalyst.

13 Claims, No Drawings

DUAL CATALYST SEQUENTIAL METHOD FOR PRODUCTION OF SORBITOL FROM HYDROLYZED STARCH SOLUTION

BACKGROUND OF THE INVENTION

1. Field of the Invention

The invention relates to a process for production of sorbitol from hydrolyzed starch solution by a two-step hydrogenation employing Raney nickel catalyst under neutral to mildly acidic conditions followed by use of a ruthenium catalyst under more acidic conditions.

2. Description of the Prior Art

Processes for production of sorbitol by hydrogenation of glucose in aqueous solution are well known in the art. For example, U.S. Pat. Nos. 3,538,019, 3,670,035 and Faith, Keyes and Clark, "Industrial Chemicals," Lowenheim et al., editors, Wiley-Interscience, New York, 4th edition, 1975, pp. 774-778, disclose the use of Raney nickel and supported nickel catalysts for commercial production of sorbitol from glucose syrups.

Ruthenium on various support materials is also known to be an effective catalyst for conversion of glucose to sorbitol from the disclosures of U.S. Pat. Nos. 2,868,847; 3,963,788; 3,963,789; 4,380,679 and W. German Application No. 3,144,320.

In a recent review by Kieboom and van Bekkum in "Starch Conversion Technology," van Beynum and Roels, editors, M. Dekker, Inc., New York 1985, page 278, typical conditions for a batch process for the manufacture of sorbitol by hydrogenation of glucose using a nickel catalyst are given as: 45-50% (w/v) aqueous solution of glucose, 120°-150° C., 30-70 atmospheres hydrogen, pH 5-6, with 3 to 6% Raney nickel based on glucose. In continuous processes higher hydrogen pressures such as 170 atmospheres, with a supported nickel catalyst are typical.

While nickel catalysts are relatively inexpensive, they suffer from the disadvantages of requiring large amounts of catalyst which can not be readily recycled to the next batch without reprocessing, and the fact that the hydrogenation is best carried out at a nearly neutral pH. Under these neutral pH conditions the residual oligosaccharides present in inexpensive glucose syrups (such as those obtained by starch hydrolysis) are not hydrolyzed to glucose, but are hydrogenated to give high levels of reduced oligosaccharides in the product.

Ruthenium catalysts are more expensive than nickel catalysts but are known to require considerably less on a weight basis for each batch. They have been known to be recycled for a few runs, but then the catalyst must be regenerated or the ruthenium metal recovered and fresh catalyst prepared.

While hydrogenation of glucose to form sorbitol in solutions at pH 2.5 to 4.5 are known, a lower pH is required for reasonably fast hydrolysis of oligosaccharides in starch hydrolyzate syrups to glucose or for hydrolysis of reduced oligosaccharides during the hydrogenation. Prior attempts to use ruthenium catalysts at a pH below 2.5 have resulted in loss of activity of the catalyst after several runs.

The term "polysaccharide" as used herein includes those saccharides containing more than one monosaccharide unit. This term also incompasses the subclass of oligosaccharides which contain, for the purposes of this specification, from two to about ten monosaccharide units. Examples of oligosaccharides are the disaccharides maltose, lactose, cellobiose and sucrose; and typical trisaccharides are raffinos and maltotriose. Hydrolysis of a disaccharide such as maltose provides two molecules of glucose per molecule of maltose. Likewise, complete hydrolysis of each molecule of the trisaccharide maltotriose provides three molecules of glucose and maltotetraose provides four glucose molecules.

Hydrogenation of an oligosaccharide such as maltose, maltotriose, maltotetraose or high oligomers of glucose (which are ordinarily present at levles from about 2-5 percent in commercially available, low cost, starch hydrolyzates such as those provided in U.S. Pat. No. 4,107,363) lead to a reduced oligosaccharide in which only the terminal aldehyde or hemiacetal groups are reduced. Thus, maltose is reduced to maltitol or isomaltitol maltotriose to a diglucosyl-sorbitol (maltriol) and the linear glucose tetramer is reduced to the corresponding triglucosylsorbitol. Hydrolysis of a reduced diaccharide molecule such as maltitol gives rise to one molecule of glucose and one molecule of sorbitol, while hydrolysis of the reduced trisaccharide, maltrotriol, affords two molecules of glucose and one of sorbitol for each molecule of maltotriol.

In the prior art methods for production of sorbitol substantial levels of reduced oligosaccharides, approximately equivalent to the level of oligosaccharide present in the starch hydrolyzate employed as starting material, are obtained.

Ordinarily, the starting material for commercial manufacture of sorbitol is either pure glucose or a less expensive starch hydrolyzate. Typical such starch hydrolyzates are those disclosed in U.S. Pat. No. 4,017,363 which provide glucose syrups of 98% or higher purity.

The glucose or dextrose content of glucose solutions or syrups can be expressed in terms of the % dextrose or as the Dextrose Equivalent (DE). The latter term is more commonly employed with starch hydrolyzates and is preferred herein.

The DE of a substance is defined as $$\frac{100 \times \text{weight of reducing sugar calculated as dextrose}}{\text{dry weight of the substance}}.$$

Low cost starch hydrolyzates obtained from corn or wheat starch are readily available in commerce. The preferred starch hydrolyzates for production of sorbitol by prior art methods are corn starch hydrolyzates having a DE of 95 or higher.

SUMMARY OF THE INVENTION

The present invention provides a process for production of sorbitol from aqueous glucose solutions, obtained by hydrolysis of starch, having a dextrose equivalent (DE) of from 50 to 98.5 which has decided advantages over the prior art. Said process comprises the steps of (a) hydrogenations of said hydrolyzed starch solution in the presence of a catalyic amount of nickel at a pH in the range of 3.0 to 7.0, at 120° to 160° C. and a pressure of from 500 to 2000 psig (35 to 140 bars), until the reducing sugar content of the mixture is below 5 percent;

(b) of nickel catalyst and acidification of the resulting solution to a pH of from 1.0 to 2.5;

(c) hydrogenation of the acidified crude sorbitol solution in the presence of a catalytic amount of ruthenium at 100° to 180° C. and a pressure of 500 to 2000 psig (35 to 140 bars) until hydrogen uptake is substantially complete, and removal of said ruthenium.

While a variety of nickel catalysts known in the art to efficiently hydrogenate glucose to sorbitol can be employed in the invention process, e.g., nickel powder, nickel on kieselguhr or other filter aid, or various nickel alloys, a preferred nickel catalyst is the well-known activated nickel-aluminum alloy, Raney nickel. Likewise, a variety of ruthenium catalysts can be employed, including, for example, ruthenium powder, ruthenium on various support materials such as carbon, alumina, silica or montmorillonite; however, a preferred such catalyst is ruthenium-on-carbon for reasons of economy and efficiency.

The invention process provides a method for production or sorbitol that has surprising advantages over the prior art. The partial hydrogenation of glucose over the less expensive nickel catalyst at near neutral pH removes components which would ordinarily deactivate or poison a ruthenium catalyst. As a result, the expensive ruthenium catalyst retains its activity from batch to batch and can be recycled numerous times. For example, after 70 hydrogenation cycles without any addition of fresh ruthenium catalyst, no evident loss of activity was observed. Another advantage of the invention process is that the aqueous acidic conditions employed in the second hydrogenation effects hydrolysis of residual polysaccharides and oligosaccharides to glucose and hydrolysis of reduced polysaccharides and oligosaccharides to glucose and sorbitol, and the glucose formed thereby is further hydrogenated to sorbitol. Thus, more complete conversion of glucose and its oligomers are obtained than was possible by prior methods.

A further advantage of the instant process is that it can be used with incompletely hydrolyzed starch solutions (for example, those having a DE of only about 50) and still give a product which is nearly completely converted to sorbitol. Use of such incompletely hydrolyzed starch solutions with the prior art hydrogenation methods gives rise to a sorbitol product having high levels of oligosaccharide and/or reduced oligosaccharides.

An especially preferred starting material for the instant process is hydrolyzed starch solution of 95 to 98.5 DE and an especially preferred starch hydrolyzate is one derived from corn starch for reasons of efficiency and economy.

DETAILED DESCRIPTION OF THE INVENTION

In carrying out the initial step of the invention process the starting glucose syrup is contacted with hydrogen in the presence of a catalytic amount of nickel.

While the starting glucose solution can be relatively dilute, i.e., as low as 20% w/v glucose, higher concentrations are preferred in order to obtain more of the desired sorbitol in each run. Thus, solutions or syrups of about 50 to 70 % w/v solids and having a Dextrose Equivalent of from 50 to 98.5 are preferred. An especially preferred such hydrolyzed starch solution is one which contains about 60% w/v total solids, for at this concentration one obtains optimum throughput of glucose per run coupled with ease of handling the starting solution and product. At higher levels of total solids, handling is less convenient since both the starting solution and product are considerably more viscous.

The pH of the starting glucose syrup is ordinarily within the range of 3.0 to 7.0, but if outside this range, the pH is adjusted accordingly by means of an acid, e.g., sulfuric acid, or a base, e.g., sodium hydroxide.

The nickel catalyst employed in the first step can be any of a wide variety of nickel catalysts known to be effective in hydrogenation of glucose to sorbitol. Examples of such nickel catalysts include nickel powder or nickel supported on various powdered or granular supports such as kieselguhr and alumina, or alloys of nickel and aluminum, all of which are known in commerce. An especially preferred such catalyst is one of the activated nickel-aluminum alloys known in the art as Raney nickel, a discussion of which is given in "Catalytic Processes and Proven Catalysts," by C. L. Thomas, Academic Press, New York, 1970, pp. 126–130. As noted above, in both hydrogenation steps the amount of catalyst employed is a "catalytic amount."

While the catalytic amount of nickel catalyst may vary over a considerable range, it is usually desirable to employ the least amount of nickel that will give optimum or near optimum results. Thus, ordinarily, from about 1.5 to 7 percent by weight of nickel catalyst is employed in the first step. When the preferred Raney nickel catalyst is used, a preferred catalytic amount is from 2 to 5% by weight of 50% wet catalyst per weight of starting 50 to 98.5 DE starch hydrolyzate solution.

As is well-known in the art, a wide range of temperatures and pressures can be employed to hydrogenate glucose over nickel catalysts. For example, temperatures of from about 100° to 180° C. and pressures of from about 20 to 200 bars (300 to 3000 psig) can be employed with satisfactory results. However, a preferred temperature is in the range of 120° to 160° C. and a preferred pressure is from 35 to 140 bars (500 to 2000 psig) and especially preferred conditions are 140°–150° C. and 70 to 90 bars. When the preferred conditions are employed, the first step is usually complete in from one to two hours.

The completion of the first step hydrogenation is determined by trial runs in which the time required under the operating conditions employed gives a crude sorbitol syrup having a reducing sugar content below about 5%, and preferably below 1.0%; typically from about 0.1 to 0.9% reducing sugars as determined by the method of Munson and Walker, *J. Amer. Chem. Soc.* 28, 663 (1906), or by the Glucose Analyzer method of U.S. Pat. No. 3,539,455.

When the first hydrogenation is completed, the nickel catalyst is removed, for example, by filtration. The clarified solution from the nickel hydrogenation is then acidified to a pH in the range of from 1.0 to 2.5. An even more preferred range is pH 1.5 to 2.0 and especially preferred is a pH of 1.7 to 1.9. While the acidification may be brought about by means of a wide variety of acids, preferred acids are those that do not attack the catalyst support or reactor materials, especially sulfuric acid or phosphoric acid.

The acidified solution is then charged to a reactor, which can be the same one used for the first hydrogenation step, or can be a different reactor or autoclave of the same type. A catalytic amount of ruthenium is added and the mixture is again hydrogenated at a temperature of from 100° to 180° C. and pressure of from about 35 to 140 bars (500 to 2000 psig) until hydrogen uptake is substantially complete.

While the amount of ruthenium catalyst employed can be varied considerably (e.g., from about 0.001 to 3% of elemental ruthenium by weight, based on weight of solids in the acidified solution), it is ordinarily a considerably smaller amount than the nickel catalyst used in the first hydrogenation step since ruthenium is well-known to be a more potent catalyst for such hydrogenations. The preferred catalysts for this step are supported ruthenium catalysts, e.g., those having an elemental ruthenium or ruthenium oxide content of from about 0.1 to 10 percent by weight of the dry catalyst, but catalysts having a higher active metal content can be used if desired. An especially preferred catalyst for this step is 5% by weight ruthenium-on-carbon. When this preferred catalyst is employed, the amount of ruthenium metal based on weight of solids in the acidified solution from the first hydrogenation step, can be from about 0.01 to 2.0% and is preferably from about 0.05 to 1.0%. Since the ruthenium catalyst can be recycled for a large number of runs (e.g., up to 70 or more runs) in the invention process, amounts of catalyst containing higher levels of ruthenium within the above ranges can be employed with little additional expense.

The second hydrogenation under acidic aqueous conditions effects hydrolysis of the residual polysaccharides, oligosaccharides and any of their reduced froms present to form additional glucose which is rapidly hydrogenated, along with any residual glucose remaining, to sorbitol. The prior hydrogenation step with nickel removes trace amounts of materials which would ordinarily poison the ruthenium catalyst after only a few runs, thus enabling the ruthenium catalyst to be recycled many more times in the present process without loss of activity.

As mentioned above, the step with ruthenium catalyst is preferably carried out at a temperature of from 100° to 180° C. and a pressure from about 35 to 140 bars (500 to 2000 psig). An especially preferred temperature is from 140° to 160° C., and an especially preferred pressure is from 70 to 90 bars (1000 to 1300 psig). Under these conditions hydrogenation is substantially complete in 2 to 3 hours or less, after which the sorbitol solution is recovered by filtration and the ruthenium catalyst is recovered for use in the next run. A particularly convenient method for this filltration is brought about by fitting the hydrogenation reactor with an externally valved pipe which terminates internally as a fritted steel disc at the bottom of the reactor, thus allowing the sorbitol solution to be removed and the catalyst to be retained in place in the reactor by merely opening the external valve arfd applying pressure to the reactor.

In a series of such runs under the conditions of the invention process the ruthenium-on-carbon catalyst has been recycled 70 times or more with no apparent loss of activity and with no further incremental addition of catalyst.

The process is further illustrated by the following examples.

EXAMPLE 1

A. To 10 kg of 60% w/v commercial hydrolyzed corn starch syrup, 95–97 DE, was added 350 g of 50% wet, Raney nickel catalyst and the resulting slurry (pH 5) was stirred under hydrogen in an autoclave at 140° C., 1400 psig (98 bar) for 85 minutes. The resulting mixture was filtered to remove catalyst. The clarified filtrate, pH 4.5, was used in the next step.

B. A sample (833 g) of filtrate containing 500 g solids was placed in a stirred autoclave and acidified to pH 1.8 with 85% phosphoric acid. To this was added 25.6 g or 50% wet 5% ruthenium/carbon catalyst (containing 0.64 g ruthenium metal), and the mixture was hydrogenated at 140° C. and 98 bar pressure for two hours. Samples were removed through a sample line equipped with a filter at 40 minutes and every 20 minutes thereafter. The ruthenium catalyst was removed by filtration. The hydrogenation was terminated at 120 minutes.

The hydrogenation with ruthenium-on-carbon was repeated, using the recycled catalyst, with three other aliquots (designated as C, D and E) of the product of Part A, but the pH in each case was adjusted to 2.0, 1.9 and 1.7, respectively, with 85% phosphoric acid. Samples were assayed for reducing sugar content (RS) by the Glucose Analyzer method*. Assays for total sugar (TS) content, oligosaccharides (DE 2–5), mannitol and iditol were by high performance liquid chromatography (HPLC).

See, for example, U.S. Pat. Nos. 3,539,455, 3,979,274 4,073,713. The instrument employed was a YSI Model 27A Industrial Analyzer from Yellow Springs Instrument Co., Inc., Yellow Springs, Ohio 45387.

The HPLC analysis was carried out on a strong acid cation exchange column in the calcium form and distilled water as the mobile phase. This separated sorbitol, mannitol, maltitol and other polyols. The components were detected with a differential refractometer and compared to an external mannitol standard. The portion of each component capable of generating glucose upon hydrolysis was calculated by applying correction factors to each component. Total sugars by HPLC on dry solids basis was obtained by multiplying the HPLC values for the reduced oligosaccharides by an empirical factor related to their glucose content upon hydrolysis (DP-2×0.5, DP-3×0.66, DP-4×0.75, DP-5×0.85). Total sugars by HPLC was obtained by summing the individual values and multiplying by 0.6. Total sugars are expressed as a 70% solution of solids by multiplying total sugars (100% basis) by 0.7.

* Empirically derived from value for total sugars by the Munson-Walker assay, *J. Amer. Chem. Soc.*, 28, 663 (1906).

TABLE I

| Ru/C-Acid Catalyzed Hydrolysis/Hydrogenation of Sorbitol Syrup From Part A* | | | | | | | | | |
|---|---|---|---|---|---|---|---|---|---|
| Sample | Time, Minutes | DP-2 | DP-3 | DP-4 | DP-5+ | % TS @ 70% | % Mannitol | % Iditol | Final pH | % RS |
| A |  | 3.68 | 0.98 | 0.27 | 0.98 | 1.48 | 0.25 | 0.12 | 4.75 | 0.09 |
| B | 40 | 2.22 | 0.46 | 0.14 | 0.20 | 0.71 | 0.51 | 0.21 | 1.8 | 0.11 |
|  | 60 | 2.11 | 0.32 | 0.08 | 0.20 | 0.63 | 0.62 | 0.29 | 1.8 | 0.11 |
|  | 80 | 1.99 | 0.23 | 0.06 | 0.14 | 0.55 | 0.76 | 0.37 | 1.8 | 0.10 |
|  | 100 | 1.85 | 0.17 | 0.03 | 0.08 | 0.47 | 0.91 | 0.47 | 1.8 | 0.04 |
|  | 120 | 2.01 | 0.21 | 0.06 | 0.27 | 0.60 | 1.09 | 0.60 | 1.8 | 0.05 |
| C | 40 | 4.11 | 0.64 | 0.18 | 0.48 | 1.27 | 0.49 | 0.33 | 2.0 | 0.11 |
|  | 60 | 2.50 | 0.49 | 0.18 | 0.35 | 0.84 | 0.65 | 0.34 | 2.0 | 0.12 |
|  | 80 | 2.27 | 0.42 | 0.14 | 0.29 | 0.74 | 0.78 | 0.41 | 2.0 | 0.11 |
|  | 100 | 2.16 | 0.37 | 0.13 | 0.34 | 0.72 | 0.93 | 0.50 | 2.0 | 0.05 |
|  | 120 | 2.07 | 0.31 | 0.10 | 0.27 | 0.66 | 1.09 | 0.60 | 2.0 | 0.05 |
| D | 40 | 2.62 | 0.57 | 0.19 | 0.58 | 0.97 | 0.55 | 0.27 | 1.9 | 0.09 |
|  | 60 | 2.36 | 0.44 | 0.16 | 0.28 | 0.77 | 0.65 | 0.34 | 1.9 | 0.09 |
|  | 80 | 2.17 | 0.38 | 0.13 | 0.22 | 0.68 | 0.79 | 0.40 | 1.9 | 0.08 |

TABLE I-continued

Ru/C-Acid Catalyzed Hydrolysis/Hydrogenation of Sorbitol Syrup From Part A*

| Sample | Time, Minutes | DP-2 | DP-3 | DP-4 | DP-5+ | % TS @ 70% | % Mannitol | % Iditol | Final pH | % RS |
|---|---|---|---|---|---|---|---|---|---|---|
|   | 100 | 2.06 | 0.33 | 0.10 | 0.22 | 0.64 | 0.93 | 0.51 | 1.9 | 0.08 |
|   | 120 | 2.04 | 0.28 | 0.10 | 0.26 | 0.63 | 1.07 | 0.59 | 1.9 | 0.08 |
| E | 40 | 2.49 | 0.45 | 0.12 | 0.24 | 0.77 | 0.52 | 0.31 | 1.7 | 0.11 |
|   | 60 | 2.34 | 0.35 | 0.08 | 0.14 | 0.66 | 0.63 | 0.38 | 1.7 | 0.10 |
|   | 80 | 2.06 | 0.22 | 0.05 | 0.05 | 0.53 | 0.71 | 0.45 | 1.7 | 0.10 |
|   | 100 | 2.02 | 0.20 | 0.04 | 0.05 | 0.51 | 0.85 | 0.54 | 1.7 | 0.09 |
|   | 120 | 2.02 | 0.19 | 0.03 | 0.06 | 0.51 | 1.00 | 0.63 | 1.7 | 0.07 |

*DP-2, DP-3, DP-4, DP-5 are reduced oligosaccharides having the degree of polymerization of 2-5, respectively.
TS = Total sugars.
RS = Reducing sugars.

EXAMPLE 2

A. The procedure of Example 1, Part A, was repeated but hydrogenation was stopped after 55 minutes and the Raney nickel catalyst removed by filtration. Samples of the filtrate containing 1.58% total sugars were used in Part B.

B. Samples of filtrate from Part A containing 500 g solids were hydrogenated using the same recycled ruthenium catalyst from Example 1. Temperature of the hydrogenation was varied from 140° to 160° C. and pH 1.7 to 2.3. The results are summarized in Table II.

(50% wet) was hydrogenated in an autoclave at 77 bar (1100 psig) with stirring at 750 rpm at 140° C. for 55 minutes. The resulting crude sorbitol syrup was removed by filtration. It was found to contain 0.40% reducing sugars and 1.63% total sugar.

B. A series of runs were made with 833 g of the syrup from Part A (500 g solids). The syrup was adjusted to pH 1.8 by addition of either concentrated phosphoric acid or concentrated sulfuric acid and at a temperature of from 140° to 160° C. employing in each run the recycled ruthenium/carbon catalyst from Example 2 containing 0.64 g ruthenium metal. Hydrogenation was

TABLE II

Ru/C-Acid Catalyzed Hydrolysis/Hydrogenation of Sorbitol Syrup From Part A

| Time, Minutes | DP-2 | DP-3 | DP-4 | DP-5+ | % TS @ 70% | % Mannitol | % Iditol | Final pH | Temp., °C. | % RS | Recycle No. For Ru/C |
|---|---|---|---|---|---|---|---|---|---|---|---|
| Part A | 3.77 | 0.78 | 0.47 | 1.19 | 1.58 | 0.27 | 0.14 | 4.4 |   | 0.72 |   |
| 60 | 2.10 | 0.36 | 0.28 | 0.23 | 0.71 | 0.59 | 0.26 | 1.7 | 140 | 0.12 |   |
| 80 | 2.04 | 0.30 | 0.25 | 0.14 | 0.64 | 0.71 | 0.31 | 1.7 |   | 0.10 | 19 |
| 100 | 1.94 | 0.23 | 0.31 | 0.09 | 0.60 | 0.81 | 0.36 | 1.7 |   | 0.11 |   |
| 120 | 1.92 | 0.19 | 0.24 | 0.24 | 0.62 | 0.92 | 0.45 | 1.7 |   | 0.06 |   |
| 20 | 1.85 | 0.26 | 0.10 | 0.10 | 0.53 | 0.83 | 0.42 | 1.8 | 160 | 0.07 |   |
| 40 | 1.54 | 0.15 | 0.03 | 0.13 | 0.46 | 1.20 | 0.66 | 1.8 |   | 0.08 |   |
| 60 | 1.61 | 0.14 | 0.03 | 0.14 | 0.43 | 1.57 | 0.91 | 1.8 |   | 0.09 | 21 |
| 80 | 1.85 | 0.11 | 0.02 | 0.57 | 0.63 | 1.96 | 1.20 | 1.8 |   | 0.08 |   |
| 100 | 2.13 | 0.14 | 0.02 | 0.27 | 0.59 | 2.50 | 1.55 | 1.8 |   | 0.08 |   |
| 120 | 2.46 | 0.12 | — | 0.11 | 0.51 | 2.98 | 1.89 | 1.8 |   | 0.07 |   |
| 20 | 2.25 | 0.48 | 0.15 | 0.39 | 0.79 | 0.82 | 0.42 | 2.0 | 160 | 0.07 |   |
| 40 | 1.93 | 0.28 | 0.07 | 0.16 | 0.57 | 1.10 | 0.61 | 2.0 |   | 0.07 |   |
| 60 | 1.80 | 0.20 | 0.06 | 0.22 | 0.53 | 1.42 | 0.83 | 2.0 |   | 0.07 | 22 |
| 80 | 1.75 | 0.13 | 0.02 | 0.15 | 0.46 | 1.85 | 1.07 | 2.0 |   | 0.07 |   |
| 120 | 1.53 | 0.08 | 0.06 | 0.42 | 0.51 | 2.16 | 1.33 | 2.0 |   | 0.06 |   |
| 20 | 2.91 | 0.58 | 0.19 | 0.46 | 1.00 | 0.68 | 0.35 | 2.3 | 160 | 0.07 |   |
| 40 | 2.57 | 0.49 | 0.16 | 0.31 | 0.84 | 0.93 | 0.52 | 2.3 |   | 0.07 | 23 |
| 60 | 2.24 | 0.40 | 0.13 | 0.23 | 0.70 | 1.15 | 0.65 | 2.3 |   | 0.06 |   |
| 80 | 2.03 | 0.34 | 0.10 | 0.21 | 0.62 | 1.49 | 0.90 | 2.3 |   | 0.06 |   |
| 40 | 2.32 | 0.50 | 0.15 | 0.32 | 0.79 | 0.66 | 0.31 | 2.0 | 150 | 0.09 |   |
| 60 | 2.03 | 0.34 | 0.09 | 0.19 | 0.62 | 0.81 | 0.40 | 2.0 |   | 0.08 | 24 |
| 80 | 1.95 | 0.25 | 0.13 | 0.17 | 0.58 | 1.02 | 0.54 | 2.0 |   | 0.07 |   |
| 100 | 1.90 | 0.22 | 0.07 | 0.38 | 0.62 | 1.22 | 0.67 | 2.0 |   | 0.07 |   |

EXAMPLE 3

A. A mixture of 50 kilograms of 60% w/w hydrolyzed starch syrup (98.5 DE) and 1000 g Raney nickel carried out at 80 bars. Samples were removed at 20 minute intervals and assayed for total sugars by HPLC and results are summarized in Table III.

TABLE III

Total and Reducing Sugars for Multiple Ru/C Catalyst Re-Use at pH 1.8

| Run | Ru/C Catalyst, Cycle No. | Temp., °C. | Acid* | % Total Sugars (HPLC) 20 | 40 | 60 | 80 | % Reducing Sugars (GA) 20 | 40 | 60 | 80 |
|---|---|---|---|---|---|---|---|---|---|---|---|
| 87 | 27 | 150 | P | 0.94 | 0.68 | 0.63 | 0.57 | 0.11 | 0.09 | 0.08 | 0.07 |
| 88 | 28 | 155 | P | 0.66 | 0.52 | 0.56 | 0.42 | 0.11 | 0.11 | 0.10 | 0.10 |
| 89 | 29 | 150 | S | 0.96 | 0.80 | 0.71 | 0.63 | 0.10 | 0.09 | 0.08 | 0.08 |
| 90 | 30 | 155 | S | 0.60 | — | 0.39 | 0.42 | 0.11 | 0.09 | 0.09 | 0.09 |
| 91 | 31 | 140 | S | — | — | — | — | 0.10 | 0.10 | 0.09 | 0.08 |
| 92 | 32 | 140 | S | — | — | — | — | — | 0.08 | — | — |
| 93 | 33 | 140 | S | — | — | — | — | — | 0.09 | — | — |
| 94 | 34 | 155 | S | — | 0.65 | — | — | — | 0.08 | — | — |
| 95 | 35 | 155 | S | — | 0.62 | — | — | — | 0.07 | — | — |

TABLE III-continued

Total and Reducing Sugars for Multiple Ru/C Catalyst Re-Use at pH 1.8

| Run | Ru/C Catalyst, Cycle No. | Temp., °C. | Acid* | % Total Sugars (HPLC) 20 | 40 | 60 | 80 | % Reducing Sugars (GA) 20 | 40 | 60 | 80 |
|---|---|---|---|---|---|---|---|---|---|---|---|
| 96 | 36 | 155 | S | — | 0.74 | — | — | — | 0.07 | — | — |
| 97 | 37 | 160 | S | — | — | — | — | — | 0.06 | — | — |

*P = phosphoric acid, S = sulfuric acid.

EXAMPLE 4

Fourteen additional runs were carried out by the method described in the previous Examples (catalyst recycle No. 38-53) employing a crude Raney nickel reduced syrup (60% w/w) having a reducing sugar content of 1.23%. For the ruthenium-on-carbon hydrogenation, the syrup was adjusted to pH 1.8 with concentrated sulfuric acid in each run and hydrogenated at 80 bar, 160° C. for 20 minutes. In each run the filtered sorbitol syrup assayed between 0.08 to 0.10% reducing sugars. In the last run, 53rd Ru/C catalyst cycle, the reducing sugars were 0.10%. The catalyst was recovered for further recycling; it amounted to 27.8 g of 50% wet 5% Ru/C.

EXAMPLE 5

A high pressure autoclave is charged with 30 g of 50% water-wet Raney nickel, 807.8 g of corn starch hydrolyzate (60.4% solids w/v, 50 DE) and 25.5 g water. The resulting mixture (58.6% solids) is purged three times with hydrogen, (0–6 bars), then pressure checked at 77 bars (1100 psig). The agitation is set at 750 rpm and the mixture heated to 140° C. After one hour samples are taken at 30 minute intervals and assayed for reducing sugars (RS) until the RS value reached about 5% or less. At the end of the run the liquid contents are blown from the vessel through a non-filtered line, and the catalyst bed let stand for the next run.

The clarified solution from above is adjusted to pH 1.7 to 1.9 with concentrated sulfuric acid and is hydrogenated in the presence of ruthenium/carbon catalyst calculated to contain 0.15% ruthenium metal based on the weight of solids in the solution from the nickel hydrogenation, at 150° C., 80 bars hydrogen pressure until hydrogen uptake ceased, about 80 to 120 minutes. The solution is blown out of the reactor through a fritted steel filter which retains the Ru/C catalyst for the next run. The clear filtrate is concentrated in vacuo to 70% solids, of which about 98% is found to be sorbitol by HPLC analysis.

When the above procedure is repeated but starting with 80 DE hydrolyzed corn starch, the same Raney nickel catalyst to which a 1 g increment of Raney nickel is added, and employing the recycled ruthenium-on-carbon catalyst from above, the resulting solution is also found to contain about 98% sorbitol based on weight of total solids.

We claim:

1. A process for production of sorbitol from a 50 to 98.5 DE hydrolyzed starch solution which comprises the steps of
    (a) hydrogenation of said hydrolyzed starch solution in the presence of a catalytic amount of nickel at a pH in the range of 3.0 to 7.0, at 120° to 160° C. and a pressure of from 500 to 2000 psig (35 to 140 bars), until the reducing sugar content of the mixture is below 5 percent;
    (b) removal of nickel catalyst and acidification of the resulting solution to a pH in the range of 1.0 to 2.5;
    (c) hydrogenation of the acidified solution in the presence of a catalystic amount of ruthenium at 100° to 180° C. and a pressure of from 500 to 2000 psig (35 to 140 bars) until hydrogen uptake is substantially complete, and removal of said ruthenium.

2. A process according to claim 1, step (a), wherein said nickel catalyst is Raney nickel.

3. A process according to claim 2 wherein said temperature in step (a) is from 140° to 150° C.

4. A process according to claim 3 wherein said pressure is from 70 to 90 bar.

5. A process according to claim 1, step (b), wherein said pH is from 1.5 to 2.0.

6. A process according to claim 5 wherein said pH is 1.7–1.9.

7. A process according to claim 1, step (b), wherein said acidification is by phosphoric acid or sulfuric acid.

8. A process according to claim 1, step (c), wherein said ruthenium catalyst is ruthenium-on-carbon.

9. A process according to claim 8 wherein said temperature in step (c) is from 140° to 160° C.

10. A process according to claim 1 wherein said hydrolyzed starch solution is 95 to 98.5 DE.

11. A process according to claim 1 which comprises the steps of
    (a) hydrogenation of hydrolyzed starch solution of 95 to 98.5 DE in the presence of a Raney nickel catalyst at a pH in the range of 3.0 to 7.0, at 140°–150° C., 70 to 90 bars pressure, until the reducing sugar content is below 1.0 percent;
    (b) removal of Raney nickel catalyst by filtration and acidification of the filtrate with phosphoric acid or sulfuric acid to a pH of from 1.7 to 1.9;
    (c) hydrogenation of the acidified filtrate in the presence of a ruthenium-on-carbon catalyst at 140° to 160° C. and a pressure of 70 to 90 bars until hydrogen uptake is substantially complete, and removal of ruthenium by filtration.

12. A process according to claim 11 wherein in step (c) a 5% ruthenium-on-carbon catalyst is employed.

13. A process according to claim 11 wherein said ruthenium catalyst is recycled.

* * * * *

UNITED STATES PATENT AND TRADEMARK OFFICE
CERTIFICATE OF CORRECTION

PATENT NO. : 4,694,113

DATED : September 15, 1987

INVENTOR(S) : Gauthier, et al.

It is certified that error appears in the above-identified patent and that said Letters Patent is hereby corrected as shown below:

Col. 1, line 64: "incompasses" should read -- encompasses --;

Col. 2, line 1: "raffinos" should read -- raffinose --;

Col. 2, line 9: "levles" should read -- levels --;

Col. 2, line 12: "4,107,363" should read -- 4,017,363 --;

Col. 2, line 16: after "isomaltitol" insert -- , --;

Col. 2, lines 15-16: "maltriol" should read -- maltotriol --;

Col. 2, line 18: "diaccharide" should read -- disaccharide --;

Col. 2, lines 20-21: "maltrotriol" should read -- maltotriol --;

Col. 2, line 62: after "(b)" insert -- removal --;

Col. 3, line 14: "or" should read -- of --;

Col. 5, line 20: "froms" should read -- forms --;

Col. 5, line 29: after "the" insert -- hydrogenation --;

Col. 5, line 39: "filltration" should read -- filtration --;

UNITED STATES PATENT AND TRADEMARK OFFICE
CERTIFICATE OF CORRECTION

PATENT NO. : 4,694,113

DATED : September 15, 1987

INVENTOR(S) : Gauthier, et al.

It is certified that error appears in the above-identified patent and that said Letters Patent is hereby corrected as shown below:

Col. 6, line 32:  insert -- * -- before "see" and after "3,979,274" insert -- and --;

Col. 6, line 48:  after "0.6" insert -- * --; and

Col. 10, line 23: "catalystic" should read -- catalytic --.

Signed and Sealed this

Twenty-third Day of February, 1988

Attest:

DONALD J. QUIGG

*Attesting Officer*  *Commissioner of Patents and Trademarks*